(12) United States Patent
Saunders

(10) Patent No.: US 7,851,229 B2
(45) Date of Patent: Dec. 14, 2010

(54) TWO-PHASE OPTICAL ASSAY WITH UNITIZED CONTAINER AND DOUBLE OR SINGLE SENSOR SYSTEMS

(75) Inventor: Alexander Michael Saunders, San Carlos, CA (US)

(73) Assignee: Primus Corporation, Kansas City, MO (US)

( * ) Notice: Subject to any disclaimer, the term of this patent is extended or adjusted under 35 U.S.C. 154(b) by 215 days.

(21) Appl. No.: 11/459,190

(22) Filed: Jul. 21, 2006

(65) Prior Publication Data

US 2007/0264718 A1    Nov. 15, 2007

Related U.S. Application Data

(60) Provisional application No. 60/799,590, filed on May 12, 2006.

(51) Int. Cl.
 *G01N 33/543* (2006.01)
(52) U.S. Cl. .................... 436/518; 435/7.1; 435/7.92; 436/523
(58) Field of Classification Search .............. 435/6, 435/7.1, 7.92–7.95; 436/164, 172, 501, 518, 436/523, 524

See application file for complete search history.

(56) References Cited

U.S. PATENT DOCUMENTS

| 4,409,335 | A | * | 10/1983 | Hanamoto et al. | ............ 436/67 |
| 5,369,037 | A | * | 11/1994 | Hansen | ....................... 436/533 |
| 5,674,699 | A | * | 10/1997 | Saunders et al. | ........... 435/7.93 |
| 6,294,342 | B1 | * | 9/2001 | Rohr et al. | ................... 435/7.1 |

* cited by examiner

*Primary Examiner*—Melanie Yu
*Assistant Examiner*—Gary W Counts
(74) *Attorney, Agent, or Firm*—Hovey Williams LLP

(57) ABSTRACT

Improved single-container, two-phase optical assays for analytes are provided which are faster and require less steps than conventional two phase optical assays. The assays of the invention involve first mixing and incubating an assay mixture including a buffer, solid particles (e.g., agarose beads), an analyte-containing sample, and an affinity agent operable to bind analyte(s) to the solid particles, followed by separation of the mixture into a particle-rich phase and a substantially particle-free phase. In one aspect, the settling step is gravity-induced and is instrumentally monitored to determine when substantially full separation has occurred. Thereafter, the respective phases may be photometrically measured to obtain qualitative and/or quantitative information about the analyte(s). It has been found that measurements taken with only one sensor set before and after settling of the particle-rich fraction give scientifically valid results as a two phase optical assay.

15 Claims, 4 Drawing Sheets

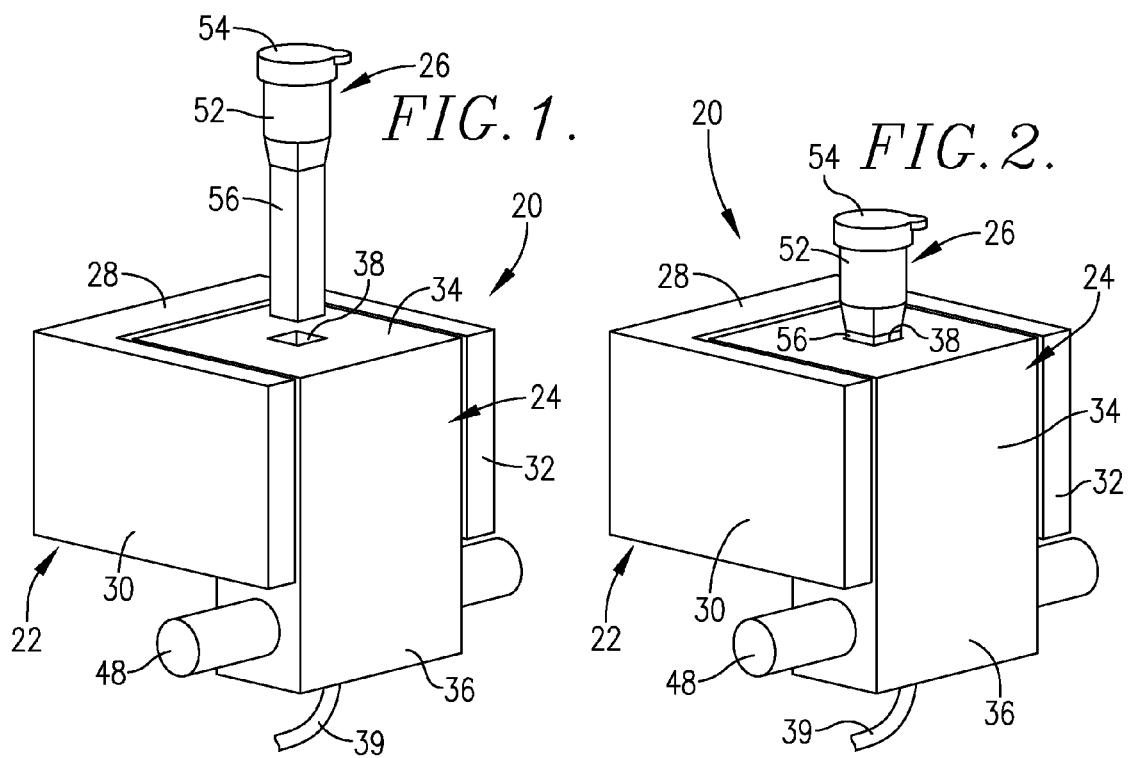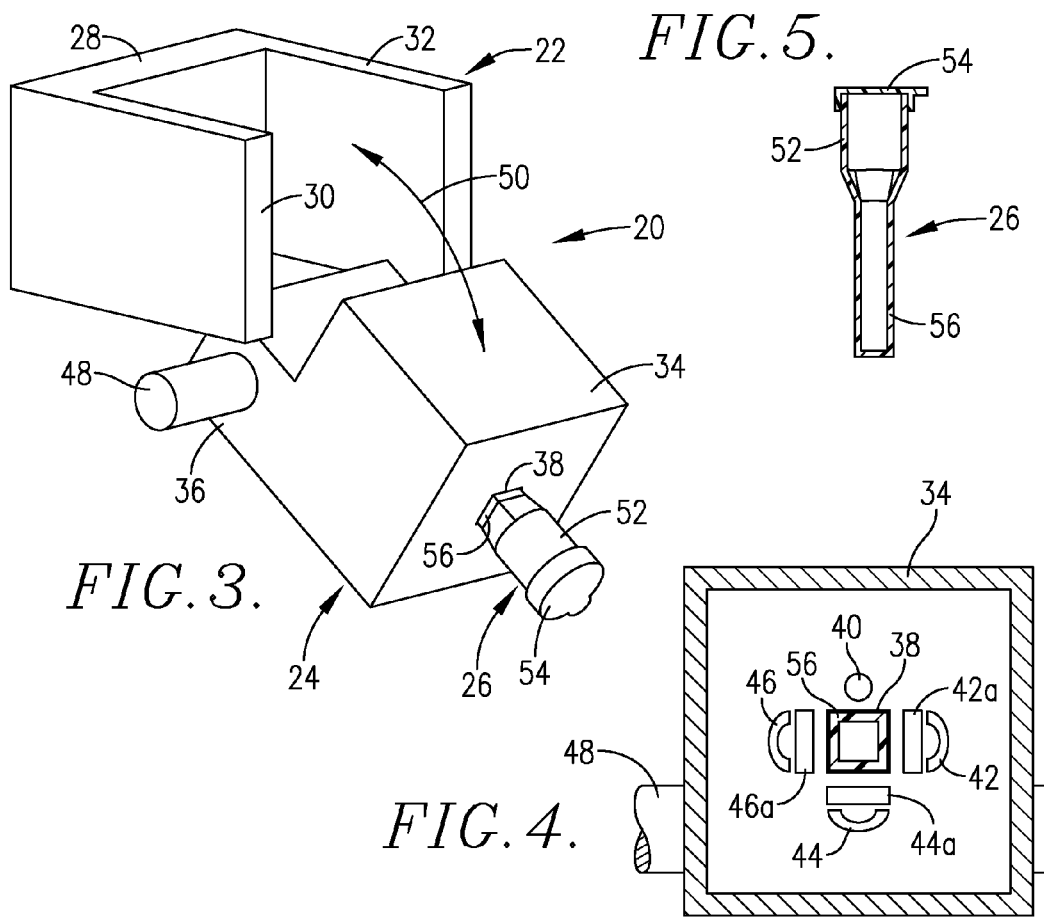

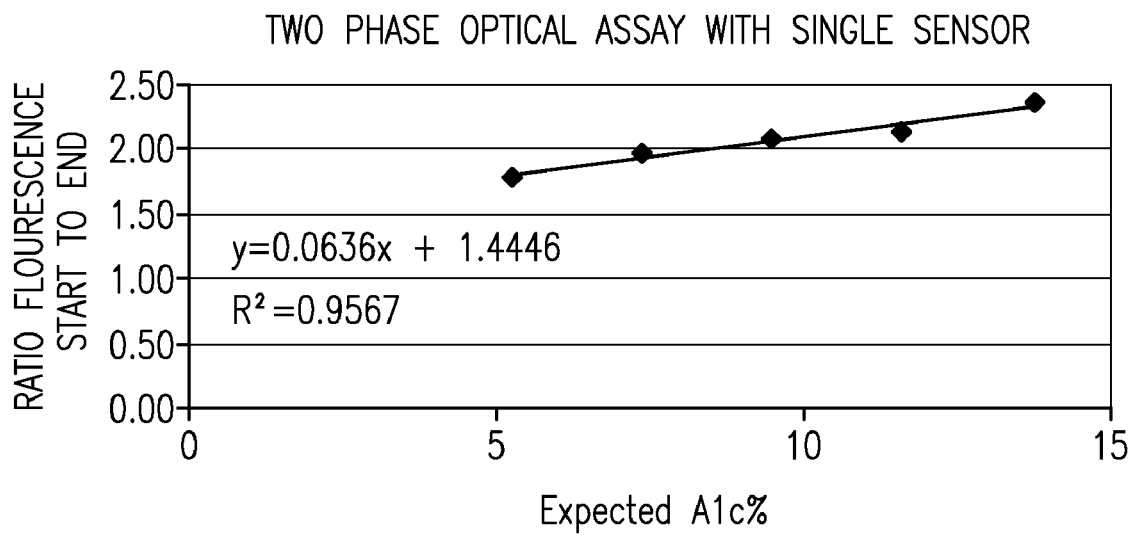
FIG.8.
FIG.9.
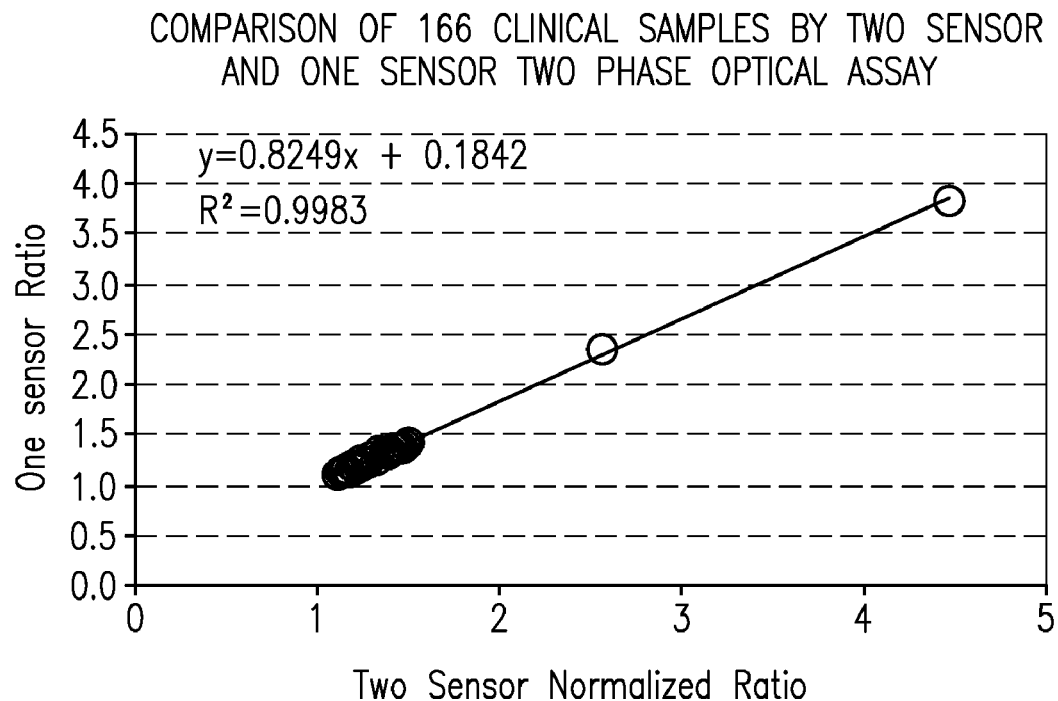

250
TWO-PHASE OPTICAL ASSAY WITH UNITIZED CONTAINER AND DOUBLE OR SINGLE SENSOR SYSTEMS

CROSS-REFERENCE TO RELATED APPLICATION

This application claims the benefit of Provisional Application Ser. No. 60/799,590 filed May 12, 2006. This Provisional Application is incorporated by reference herein.

BACKGROUND OF THE INVENTION

1. Field of the Invention

The present invention is in the field of chemical analysis usually performed along with physical separation of analytes from solution by means of a solid phase. If there are multiple analytes some remain in the solution phase and others may attach to the solid phase. The attachment is said to occur by means of ligand pairs, where one of the pair of ligands is permanently attached to the solid phase and the other of the ligand pair is a characteristic of at least one of the analytes to be detected. The separation process permits separate identification and detection of multiple analytes when the characteristic of the ligand is present on one but not all of the analyte molecule species. Common application of such phase separations is practiced in Enzyme Ligand Immuno Assay (ELISA) and in chromatography. By contrast, two phase optical assays are designed to overcome the common steps of physically separating the analytes for analysis in separate compartments by applying optical analysis to both the solid phase and the solution phase in one container.

The present invention is thus broadly concerned with improved two-phase assays normally carried out in a single container or cuvette using an assay mixture including a buffer, a plurality of particles or beads, an affinity (ligand) agent, a sample to be assayed, and a marker. More particularly, it is concerned with such assays wherein settling and phase separation of the assay mixture after incubation may be monitored to a steady state condition, whereupon assay data can be generated using a source of electromagnetic radiation in a dual sensor or single sensor system. The invention also takes advantage of timely measurements of optical phases during the settling process. The assays of the invention may also be used to identify and/or quantitate multiple analytes in a single sample.

2. Description of the Prior Art

U.S. Pat. No. 5,674,699 (incorporated by reference herein) describes the use of a suspension of affinity-specific micro beads in order to adsorb one specific ligand species out of a series that may be present in a given sample to be assayed. However, instead of eluting the specific ligand as a separate fraction, as is common in conventional chromatography, the measurement of the adhered ligand is performed while attached to the micro beads, in a special container. In order to perform these measurements, the '699 patent provides a container configured so that some of the micro beads and suspending liquid are transferred to a capillary, stoppered, and centrifuged. The capillary forms the measurement container.

Two methods are described for measuring the adhered ligand. One is by absorbance of light of a specific wavelength by the ligand. Since the micro beads are transparent, light is passed through them and only light that is absorbed by the analyte is attenuated. A second wavelength, not absorbed by the analyte, is used as an optical correction for the roundness of the capillary container and for the slight light scatter from the micro beads. A second analyte, present in the sample, but not having the specific ligand characteristic remains in the solution phase and is measured separately in the said solution phase.

The other method of measurement is fluorescence quenching, wherein a fluorescent dye which absorbs light at the same wavelength as the analytes is dissolved in the suspending liquid. Dye solution surrounds the micro beads and penetrates the micro beads to the same extent as the analyte itself. In the presence of analyte, there is less fluorescence because the light is absorbed by the analyte and is not available for excitation of the fluorescent dye. This second method is less dependent upon the complete transparency of the micro beads, but is nevertheless linearly related to the amount of analyte present both in the supernatant, solution phase, and in the micro bead lower phase, after the micro beads settle.

The apparatus and methods described in the '699 patent are specialized and somewhat cumbersome and time-consuming to use. That is, the container apparatus having the separate mixing and measuring sub-compartments, and the need for centrifugation, are limits upon the commercial utility of the assays described in this patent.

SUMMARY OF THE INVENTION

The present invention overcomes the problems outlined above and provides improved two-phase assays which are easier to perform than conventional assays of this character, while giving scientifically equivalent results. Such two-phase assays broadly include the steps of first mixing and incubating a mixture in a container, the mixture comprising a suspension of solid particles, a sample to be analyzed and having at least one analyte of interest, and an affinity agent operable to bind the at least one analyte to the particles. After mixing/incubation, the mixture is separated in the container into a particle-rich phase and a substantially particle-free phase. Thereafter, the analyte is photometrically measured (as used herein, "measured" refers to analyte identification and/or quantification).

In one aspect of the invention, the post-incubation separating step is allowed to proceed under the influence of gravity without the need for centrifugation, and is periodically monitored to assess the extent of fractionation of the mixture. This is preferably accomplished by directing electromagnetic radiation of a first wavelength through the container and mixture at respective, vertically spaced apart locations, and measuring a first parameter incident to the radiation as a measure of the extent of separation of the mixture. When the measurement of the first parameter indicates substantially complete separation of the mixture, electromagnetic radiation of a second wavelength is directed through said container and at least one of the phases, and a second parameter is determined as a measure of the at least one analyte.

Preferably, the monitoring is commenced immediately after the mixing/incubation is complete and prior to any substantial settling of the solid phase particles within the mixture. Also, in most instances, the first and second wavelengths of the incident radiation are the same, as are the first and second measured parameters (most preferably the parameters are selected from fluorescence quenching and radiation scatter).

In a second aspect of the invention, an improved two-phase assay is provided wherein, after mixing/incubation and before separation of the assay mixture, electromagnetic radiation is directed through the container, and a parameter is measured according to the radiation from a combined phase as a measure of all the analytes of the sample. Subsequently, when the particles are settled, a second measurement is recorded by the same sensor and, accordingly, the second measurement is restricted to a phase where one or more analytes are separated to the micro particles. In this fashion, data collection and analysis is simplified, yet equivalent results are obtained as compared with prior two-phase assays measuring both the particle-rich and substantially particle-free phases as an end point.

In preferred forms, the assays of the invention are carried out in a single container throughout the entire method, i.e., there is no transfer of assay mixture between containers. Additionally, the assay mixture would commonly include an optically detectable marker for the analyte(s) of interest, most preferably a fluorescence tag, such as a dye. Such a marker may be an inherent characteristic of the analyte(s), or may be chemically attached to the analyte(s), or may be freely dissolved in the solution of the assay.

In still more preferred forms of the invention, the mixing/incubation step is accomplished by repeatedly inverting the mixing/reading container in order to assure full mixing of the solid particles and liquid phase. A simplified apparatus is provided which receives a specialized capped cuvette holding the assay mixture. This apparatus is operable to repeatedly invert the cuvette for a predetermined period, and then return the cuvette to an upright position for gravity-induced settling of the assay mixture into the respective phases. The apparatus also includes a light sources and sensors for carrying out the monitoring and measurement steps.

The invention also provides a method of qualitatively determining a plurality of analytes, especially a variety of protein species. In this latter method, a buffer system containing ion exchange solid particles (e.g., carboxymethyl agarose) is employed, and the buffer is split into a plurality of different containers, each having different ionic concentrations. Samples are applied to each container and are subjected to the mixing/incubation, separation, and photometric detection steps described above. A logic scheme can then be developed to identify a number of variants, depending upon an analysis of the photometric results between the different containers. Important hemoglobin variants which can be screened in this fashion include hemoglobin F, hemoglobin A, hemoglobin S, and hemoglobin C.

BRIEF DESCRIPTION OF THE DRAWINGS

FIG. 1 is a schematic, perspective view of an analyzer in accordance with the invention, shown with a complemental sample cuvette disposed above the analyzer;

FIG. 2 is a view similar to that of FIG. 1, but showing the sample cuvette installed in the analyzer;

FIG. 3 is a view similar to that of FIG. 2, but illustrating the analyzer during tumbling of a sample;

FIG. 4 is a generally schematic, horizontal sectional view through the tumble block of the analyzer, and depicting a source of electromagnetic radiation and associated sensors disposed about the cuvette-receiving opening of the block;

FIG. 5 is a schematic, vertical sectional view of a preferred sample cuvette in accordance with the invention;

FIG. 8 is a graph of the ratio of fluorescence observed at the beginning of fractionation and after substantially complete fractionation, versus expected glycated hemoglobin, developed using a two-phase optical assay with single sensor, as described in Example 2;

FIG. 9 is a graph illustrating a comparison of analyses of clinical samples using both a two sensor and one sensor two-phase optical assay.

DETAILED DESCRIPTION OF THE PREFERRED EMBODIMENT

Figure 6:
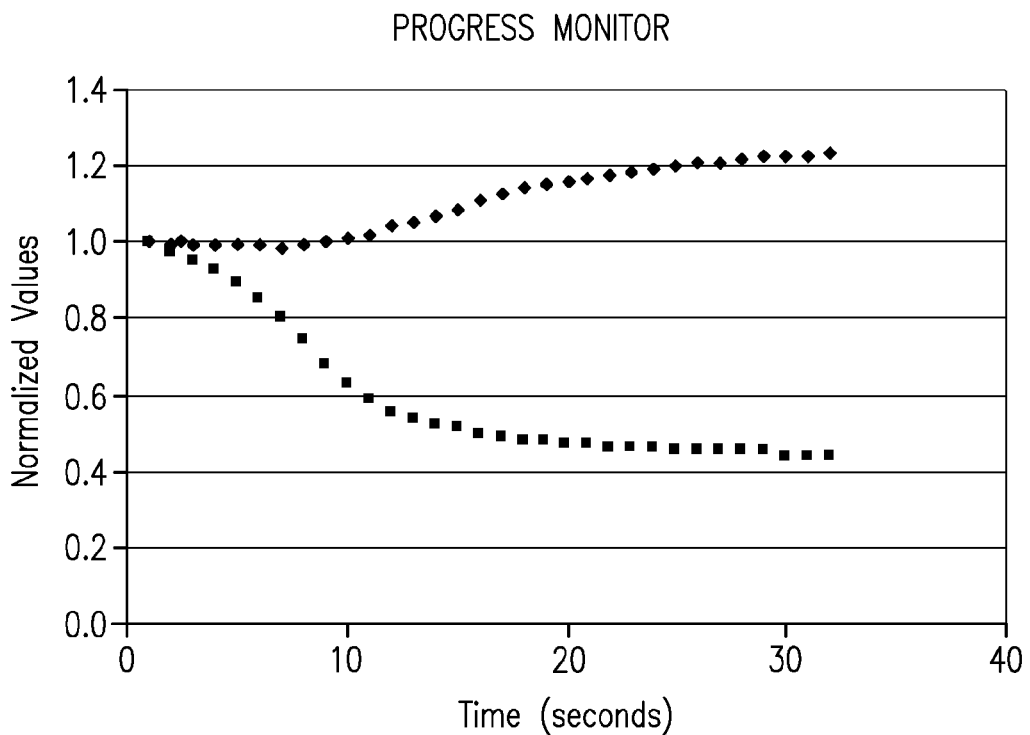
FIG. 6 is a graph depicting typical results during monitoring of fractionation of a sample during an assay in accordance with the invention.

Turning now to the drawings, a preferred analyzer 20 in accordance with the invention is depicted in FIGS. 1-3. Broadly, the analyzer 20 includes a generally U-shaped mounting block 22, a reciprocal tumbling block 24, and a specialized cuvette 26. The analyzer 20 is designed to receive a sample to be analyzed within a stoppered cuvette 26, and to effect incubation of the sample and final analysis thereof within the cuvette, avoiding any transfer of material during the course of the assay.

In more detail, the mounting block 22 has rear wall 28 and forwardly extending, spaced apart sidewalls 30, 32. The primary function of the block 22 is to provide a stable base for tumble block 24 and therefore the precise shape and dimensions of block 22 are variable. As an alternative design the mounting block 22 may contain the light sources and sensors presently shown in FIG. 4.

The tumble block 24 includes an upper, primary section 34 as well as a lower connection portion 36. The section 34 has a central, vertically-extending, substantially square in cross-section opening 38 formed therein which is designed to receive the lower end of cuvette 26. In addition, the section 34 is equipped with one or more sources 40 of electromagnetic radiation (e.g., LEDs or lasers) adjacent one face of the opening 38, along with three photo sensors 42, 44, 46 disposed adjacent the remaining three faces of opening 38. Each of the photo sensors 42-46 may optionally have a long pass filter 42a, 44a, and 46a located between the respective sensor and the cuvette opening 38. Additionally each of the sources of electromagnetic radiation and sensors may have an aperture to control the direction of the rays of the electromagnetic radiation. Appropriate electrical leads 39 extend from block 24, in order to operatively connect the internal components 40-46 to a computer or other digital processor (not shown). Specific design and combination of sources of electromagnetic radiation, sensors, filters and apertures are dependent on specific applications. In an alternate configuration all the optical components are disposed in the support block 22.

The lower connection portion 36 is pivotally coupled to the sidewalls 30, 32, as best seen in FIG. 3. In addition, a wrist pin or shaft 48 is secured to the portion 36 and is in turn operably coupled with a drive motor (not shown) operable to pivot the tumble block 24 along a path indicated by arrow 50 during the course of sample assays using analyzer 20. Also not shown is an external light tight container enclosing the complete assay assembly.

The cuvette 26 includes an upper, radially enlarged segment 52 equipped with a stopper or sealing cap 54, as well as a lower, substantially square in cross-section segment 56 complemental with opening 38. Preferably, at least the segment 56 is formed of glass or synthetic resin material which is capable of transmitting electromagnetic radiation of desired wavelength for analyses of samples using analyzer 20; most typically, the cuvette body is formed of essentially transparent material.

It will be appreciated that the apparatus illustrated in FIGS. 1-5 is exemplary only, and a variety of other possible analyzers can be used. To give but one alternative, if desired the tumble block section 34 may have appropriately sited apertures communicating with the opening 38, with a light source 40 being mounted in one of the sidewalls 30, 32 while detector(s) are mounted in the opposed sidewall. Also, the analyzer could be designed for full 360 degree rotation, as opposed to the back and forth reciprocal tumbling movement used in the illustrated embodiment.

The optical components presented in FIG. 4 may be disposed at one or more than one position along the vertical axis of tumble block 34. In at least one application optical components are disposed 2 mm and 14.5 mm above the bottom of the cuvette. In another application only the optical components 2 mm above the bottom of the cuvette are in use.

As described, the analyzer 20 is used for two-phase assays carried out in a single container or cuvette having walls formed of electromagnetic radiation-transmissible material. The assay mixture normally includes a liquid buffer, a known amount of solid particles or beads, a sample which may or may not contain analyte(s) of interest, an affinity agent (typically bound to the beads) operable to bind the analyte(s) to the beads, and a radiation-activated marker such as a fluorescent dye which activates upon incident electromagnetic radiation of known wavelength.

In the assays of the invention, the assay mixture is mixed and incubated for a period of time sufficient to effect affinity binding of analyte(s) to the beads, and to ensure essential homogeneity of the beads within the buffer. Thereafter, the mixture is allowed or caused to settle and separate into a bead-rich lower phase and a substantially bead-free upper or supernatant phase. Preferably, when using an analyzer such as that illustrated in FIGS. 1-4, a cuvette having approximately 4 mm minimum cross-section at the region of measurement is employed. The container walls in this region of measurement are flat, for optical advantage. The internal size of the cuvette is somewhat constrained by the requirements of mixing. Advantageously, a bubble should be able to pass the full length of the cuvette when it is repeatedly inverted. That is, when the closed cuvette is tumbled while containing the assay mixture and air, the micro beads are maintained in suspension and the sample is fully exposed to the beads. The ability to pass a bubble from bottom to top during tumbling is enhanced by the use of surfactants. Even with surfactants, however, it is desirable that a minimum of 3.5 mm be permitted for passage of the bubble for best mixing.

After incubation and tumbling, the cuvette is returned to an upright position and allowed to settle and fractionate under the influence of gravity. Before, during and after separation into the upper and lower phases is achieved, measurements are taken by passage of electromagnetic radiation through the mixture to obtain sensed assay data giving information about the analyte(s) and about completion of the separation of phases. Such data may be derived using a two-sensor arrangement wherein respective sensors are located at vertically spaced locations adjacent the upper phase zone and the lower phase zone. In this type of analyzer, incident radiation is directed through the container at the two spaced locations, and such is sensed by the individual sensors. In a more preferred embodiment, a single sensor arrangement is employed wherein only a single sensor is located adjacent either the upper phase zone or lower phase zone, and most preferably adjacent the latter.

The present invention includes a number of improvements over the conventional two-phase assays known in the art and described in U.S. Pat. No. 5,674,699. For example, the '699 patent preferably employs a centrifugation step in order to effect fractionation of the assay mixture into a particle-rich fraction and a particle-free fraction. In the preferred embodiment of the present invention, however, such centrifugation is eliminated and replaced by gravity-induced settling and instrumental monitoring of fractionation during the course of settling. When this settling reaches a steady state as verified by the instrumental monitoring, final assay measurements may be taken with assurance that adequate separation has been achieved.

In order to monitor the settling process on a consistent basis, measurements should begin essentially immediately upon the termination of the mixing or tumbling step. A standard profile of settling is produced if the sample is successfully settled and fractionated. The preferred profile takes into account both the disappearance of micro beads from the upper supernatant phase, and full packing of micro beads into the lower phase. FIG. 6 illustrates such a profile, in the context of a fluorescence quenching assay for glycated protein. The FIG. 6 measurements are normalized in that the ratio of the first measurements in time, taken in both the upper and lower sensors, is taken as a constant. This constant is then used as a denominator for each subsequent measurement taken at both sensors, until a final steady state is reached, as illustrated in FIG. 6, where little or no further divergence between the upper and lower data points is observed. Specifically, the diamond-shaped data points are a top or supernatant sensor settling profile, while the filled square data points represent the bottom or bead-rich phase sensor profile. As more analyte settles to the bottom, there is greater fluorescence quenching and therefore less transmitted light. In contrast, the light path of the top sensor experiences less quenching as the micro beads with concentrated analyte settled towards the bottom of the tube.

The ratio of the two final measurements is taken as representing the proportion of analyte distributed between the supernatant phase and the settled micro bead phase. In an unknown sample, this ratio may be related by comparison with ratios of at least two known standards to give the percentage of bound and unbound analyte.

A further analysis of FIG. 6 reveals that equivalent assay results may be obtained by using only the lower sensor data. This comes about by virtue of the fact that the total analyte in both the supernatant fraction and micro bead fraction is evenly distributed during the very short period when the beads are in full suspension before settling begins. Thus, if a ratio is taken between the fully suspended and settled micro beads, it is possible to derive the proportion of bound analyte to total analyte. In this single sensor mode of operation, there are fewer constraints. Thus, the requirement of matching the optical characteristics of the upper and lower measurement regions is obviated, along with matching the electronic characteristics of the two measurement positions. The elimination of these two constraints allows the use of much simpler instrumentation, while still maintaining the advantages of a two-phase assay. The two phases here are not supernatant solution and micro beads, but rather full suspension of micro beads in solution and settled micro beads measured in the same container, at the same position, but at different times. In this embodiment, one original constraint remains, i.e., the proportion of micro beads in the solution. It is this constraint that enables the calculation of proportional distribution of analyte in the two phases.

A further benefit of using a single sensor for the two-phase assay is the realization of a faster end point. The sensing area at the bottom sensor is in a steady state earlier in the settling process, because some of the smaller micro beads have not settled from the top sensor region. This observation is also illustrated in FIG. 6.

The foregoing description involves embodiments making use of fluorescence quenching. Another mode of measurement is direct fluorescence of a fluorescent analyte, or fluorescence-labeled analyte that may be specifically adsorbed onto the micro beads. For example, the proportion of glycosylated proteins may be determined in a mixture also containing non-glycosylated proteins by brief exposure of the mixture to fluorescamine, which attaches to free amino groups on both types of the protein. The non-reacted fluorescamine becomes non-fluorescent and does not further react within a few minutes of exposure to aqueous solution. The mixture is subsequently transferred to a tube containing buffer, and micro beads that attract carbohydrates and other cis-glycols, such as micro beads conjugated to aminophenyl boronic acid, as described in U.S. Pat. No. 4,269,605, incorporated by reference herein. The glycosylated proteins are attracted to the micro beads and contribute fluorescence to the micro beads, whereas non-glycosylated proteins remain in solution and contribute fluorescence to both the solution and as a background in the region of the micro beads. By the same principles of measurement, fluorescent-labeled antibodies may be used to measure the presence and/or quantity of a non-labeled analyte.

Many other assay applications are made possible by the two-phase assay of the present invention. An antibody or lectin, or indeed any other ligand, may be substituted for boronic acid affinity reagents attached to micro beads. Antibody to a hemoglobin variant, such as fetal hemoglobin, sickle cell hemoglobin, and hemoglobin C, may be used to screen for the presence of the variant. Moreover, antibodies to multiple variants of hemoglobin may be attached to micro beads all in a single container, for the general purpose of screening. Variants attached to micro beads may be further distinguished from those not attached and remaining in the solution phase. Thus, a general approximation may be made between presence only of variants in a patient and a heterozygous patient in whom some hemoglobin is normal and some is variant. Assays for the same variant hemoglobins may also be performed by use of ion exchange micro particles and varying the ionic concentration of the buffer.

The following examples set forth presently preferred equipment and process steps useful in carrying out the assays of the present invention. It is to be understood, however, that these examples are presented by way of illustration only, and nothing therein should be taken as a limitation upon the overall scope of the invention.

EXAMPLE 1

Two Sensor, Two-Phase Optical Assay Using Unitized Container

In this assay, a transparent polystyrene cuvette 26 was used having a lower segment 56 of 4 mm square cross-section. An assay mixture was placed within the cuvette, comprising 700 micro liters of buffer and 6% agarose micro beads affinity labeled with amino phenyl boronic acid, the latter in an amount totaling precisely 10% of the total volume of the mixture. The labeled beads were prepared by the method described in U.S. Pat. No. 4,269,605, incorporated by reference herein. The buffer was 50 mM glycine buffer at pH 9.2, containing 50 mM magnesium chloride, 0.1% Triton X100 surfactant, 10% reagent grade ethanol, and distilled water. The mixture also contained 0.11 mM of fluorescent dye, 8-hydroxy-3, 6,9-pyrene trisulfonate (HPT).

Calibrated samples commercialized by Primus Corporation of Kansas City, Mo., containing 5.5 and 14% glycated hemoglobin were mixed together in such proportions that five samples of known glycated hemoglobin content were prepared. These knowns are referred to as the "linearity series."

Four micro liters of one of the linearity series samples was placed in a cuvette containing the mixture described above. The cuvette was then tumbled for seven minutes by repeatedly inverting the cuvette. The cuvette was then immediately placed within a measuring device using light emitting diodes (405 nm) applied in an alternating on/off fashion to the bottom of the cuvette tube and at a position 12.5 mm above the bottom measurement point. Digitized data was then collected for a period of 3.5 minutes, until a steady state was achieved, thus establishing essentially complete fractionation of the sample into a bead-rich lower phase and a substantially bead-free upper phase. This data was then plotted to develop a normalized profile of the type illustrated in FIG. 6.

Figure 7:
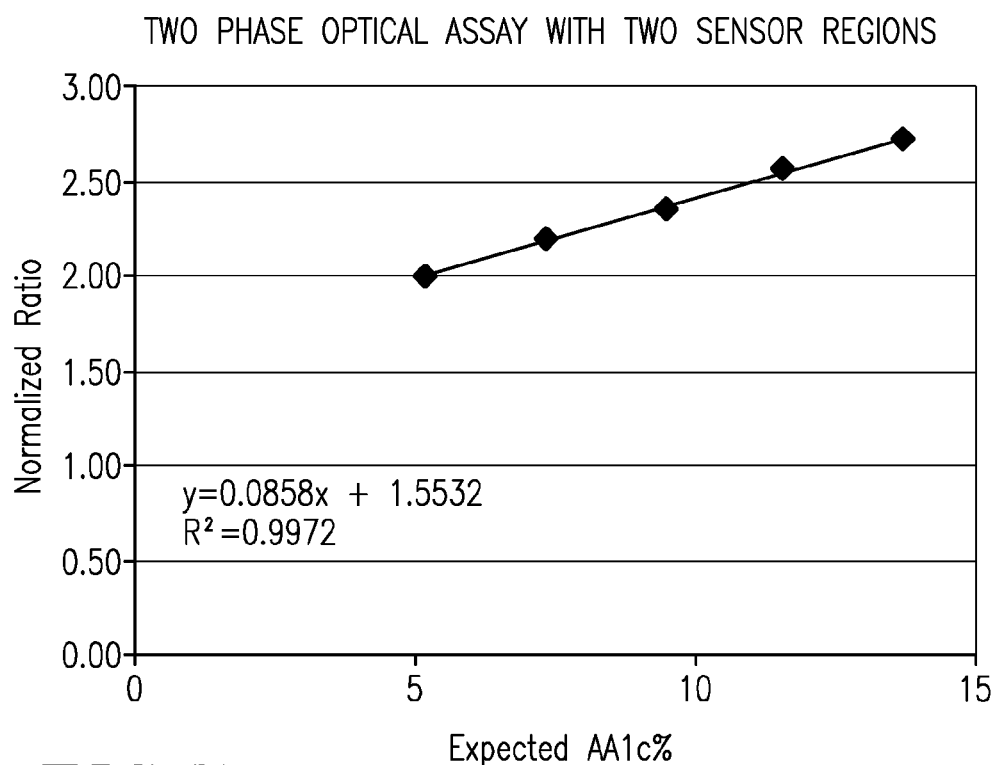
FIG. 7 is a graph illustrating the normalized ratio versus expected glycated hemoglobin, developed using a two-phase optical assay with two sensor regions, as described in Example 1.

Next, all five of the linearity series were processed in duplicate, and data recorded individually for each sample. The results are set forth in FIG. 7, which are the ratios of the upper to the bottom measurements at the end of the essentially complete separation or settling period. The FIG. 7 graph provides essentially linear results, thus confirming the validity of the assay.

EXAMPLE 2

Single Sensor, Two-Phase Optical Assay Using Unitized Container

In this example, all of the reagents and instrumentation of Example 1 were used, but with a different method of data analysis. Specifically, for this example, only data from the bottom sensor was evaluated, and the ratios developed were that of the initial fluorescence intensities observed at the bottom sensor at the conclusion of tumbling and before any substantial settling occurred, versus the final fluorescence intensities observed at the bottom sensor after complete settling. Data from the same linearity series described in Example 1 was recalculated using only the single bottom sensor data, and the result is set forth in FIG. 8. Again, the linearity of the FIG. 8 graph confirms the validity of the assay, using only the bottom sensor data.

EXAMPLE 3

Comparison of Methods Using Clinical Samples

In this example, the two data analysis methods of Examples 1 and 2 were compared in the course of running a large set (166) of clinical glycated hemoglobin samples. FIG. 9 sets forth the comparison of data together with the correlation calculations. This demonstrates that it is possible to obtain essentially equivalent results when the two-phase assay of the invention is analyzing using either the two sensor or single sensor methods.

EXAMPLE 4

Determination of Bead Concentration by Light Scattering Analysis Using a Single Sensor In this example, an LED emitting light at 650 NM was used to obtain light-scattering data. This data comprised two components, namely light loss as a result of the transmission mode where light passing from the LED to the opposite photo sensor was diminished by the presence of the beads within the sample, and by light scattering onto the photo sensors located at right angles to the LED, where the micro beads scatter light proportional to the amount of beads present. It should be noted that light from the 650 nm LED is not absorbed by the hemoglobin analyte that may be present in the sample, or by the dye, HPT, that is used to generate contrast in the fluorescent mode of evaluation descried in Example 1 and Example 2. Therefore the measurement here described may be performed in the presence of sample and the full chemical complement of the assay for analytes.

Figure 10:
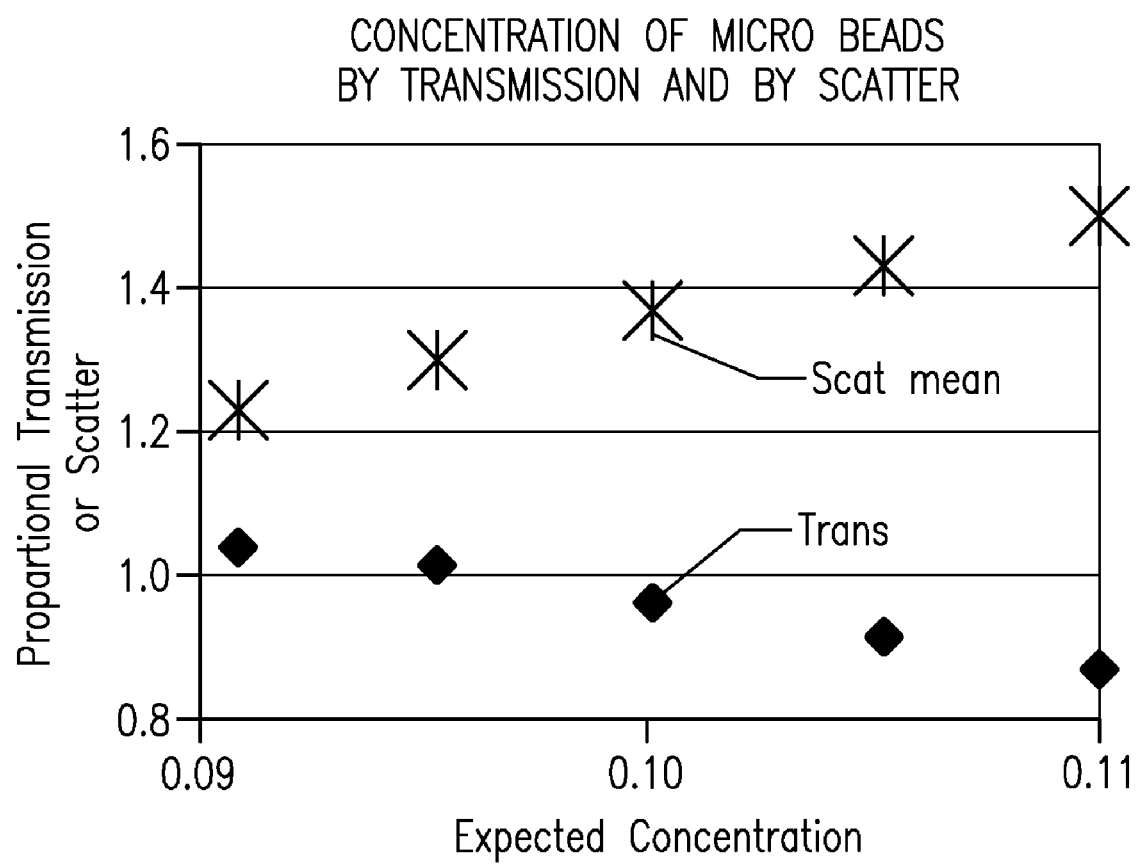
FIG. 10 is a graph of proportional transmission or scatter of radiation versus expected concentration of micro beads, as described in Example 4.

Specifically, five suspensions having from 8.3 to 12.5% micro beads in distilled water were prepared, and transmission and light scattering measurements were taken in duplicate and averaged. The collected data is set forth in FIG. 10, where it will be seen that both the transmission and scatter mean data provide linear series. This again confirms the validity of the assays of the invention. Repeating this assay and using only the upper sensor region provides substantially equivalent results.

EXAMPLE 5

Detection of Proportion of Protein as Gamma Globulin

Samples of bovine serum albumen (BSA) and bovine gamma globulin (BGG) were prepared at concentrations of 10 mg/ml in distilled water. Twenty micro liters of lisamine rhodamine sulphonyl chloride (1 mg/ml) was added to 2 ml of each protein sample, and labeling was allowed to continue for two hours at room temperature. Measurement cuvettes were prepared containing 700 micro liters of 10% agarose gel labeled with Protein G (Amersham Biosciences HiTrap Protein G HP), a known protein ligand which absorbs BGG, but not BSA. One measurement cuvette was supplemented with only BSA, a second was supplemented only with BGG, and a third was supplemented with equal volumes of BSA and BGG. Tumbling, settling, and measurement of fluorescence were carried out as described in Example 1, and the ratios of fluorescence observed from the substantially bead-free supernatant phase and the affinity-labeled, bead-rich agarose phase were calculated. These ratios are set forth below.

TABLE 1

| BSA | BGG | Fluorescence Ratio |
|---|---|---|
| 0 | 40 μL | 1.80 |
| 40 μL | 0 | 1.05 |
| 20 μL | 20 μL | 1.48 |

This data demonstrates that labeled proteins with different ligand characteristics may be distinguished by the assays of the present invention, so long as the label characteristics are known.

EXAMPLE 6

Screening Assay for Hemoglobin Variants

In this example, beads having the property of cation exchange are employed in a plurality of different containers in order to screen for hemoglobin variants. Specifically, carboxymethyl agarose is prepared using 4% cross-linked agarose. A 50 mM glycine buffer at pH 6.85 is also prepared, containing 0.1% Triton X100 and 11 μM 8-hydroxypyrene trisulphonic acid. The buffer is divided into three parts which are adjusted to sodium chloride concentrations of 0.011, 0.016, and 0.026 M, respectively. The prepared micro beads are washed in these buffers and suspensions are made of the beads at a level of 10% in the individual buffers.

Next, 10 micro liters of whole blood are added to each suspension. These samples may contain hemoglobin variants having different elutions from chromatography columns at different retention times, using gradients similar to the buffers described herein. As a screening test, the different suspensions would either retain a hemoglobin variant in the micro bead after tumbling and settling, or would permit the hemoglobin variant to remain in solution, according to Table 2:

TABLE 2

| | Buffer System | | |
|---|---|---|---|
| | 0.011 M NaCl | 0.016 M NaCl | 0.026 M NaCl |
| In Micro Beads | HbA$_0$, HbS, HbC | HbS, HbC | HbC |
| In Solution | HbF | HbF, HbA$_0$ | HbF, HbA$_0$, HbS |

The position of a particular hemoglobin variant in the micro beads or in solution is determined by the amount of hemoglobin measured by the fluorescence method of Examples 1 or 2. Thus, according to a logic scheme such as that set forth in Table 2, it is possible to determine variant types through the screening process of this Example.

In greater detail, if there is a hemoglobin variant in solution in the 0.011 M NaCl suspension, then it is a "fast moving" variant, such as HbF. If in the 0.011 M NaCl suspension there is a hemoglobin variant in the micro beads, then this cannot be distinguished as being normal HbA$_0$, HbS, or HbC. However, if in combination with such 0.011 M NaCl suspension results, there is no hemoglobin variant in the 0.016 and 0.026 M NaCl suspensions, then the presence of HbS and HbC may be ruled out. On the other hand, if all hemoglobin variants are retained in the micro beads until the highest molarity, then the presence of HbC is confirmed. Thus, both homozygous and heterozygous patients with variant hemoglobins may be distinguished.

I claim:

1. A method of measuring at least one analyte in a sample, comprising the steps of:
    incubating a mixture in a container, said mixture comprising a buffer, solid particles, said sample, and an affinity agent operable to bind the at least one analyte to said particles, and establishing a fully suspended phase where said particles are substantially uniformly distributed throughout said buffer;
    gravitationally separating said incubated fully suspended phase in said container to give a particle-rich phase;
    initially measuring a parameter of said at least one analyte in said fully suspended phase substantially at the beginning of the separating step, and subsequently measuring a parameter of said at least one analyte in said particle-rich phase at the end of the separating step, said initial and subsequent measuring steps each comprising directing electromagnetic radiation through said container; and
    using said measurement parameters to calculate the proportional distribution of said at least one analyte in said fully suspended phase and in said particle-rich phase.

2. The method of claim 1, including the step of maintaining said mixture within said container throughout all of the steps of the method.

3. The method of claim 1, said incubation step comprising the step of repeatedly inverting said container with said mixture therein.

4. The method of claim 1, including the step of monitoring said mixture during substantially the entirety of said separating step to determine the extent of phase separation thereof.

5. The method of claim 1, said measurement parameters being selected from the group consisting of fluorescence intensity, fluorescence quenching, and radiation scattering.

6. The method of claim 1, said analyte comprising a glycated protein.

7. The method of claim 6, said glycated protein being glycated hemoglobin, said agent being an affinity agent for glycated hemoglobin.

8. The method of claim 1, including the step of simultaneously measuring a plurality of analytes within said mixture.

9. The method of claim 8, said plurality of analytes comprises hemoglobin variants.

10. The method of claim 9, including the steps of using as said particles cation exchange particles within a plurality of different containers each having a buffer system with different salt concentrations.

11. The method of claim 10, said cation exchange particles comprising carboxymethyl agarose, and said hemoglobin variants are selected from the group consisting of hemoglobin F, hemoglobin A, hemoglobin S, and hemoglobin C.

12. Method of claim 8 where the plurality of analytes includes an analyte from said sample and said fully suspended phase.

13. The method of claim 1, said calculation step comprising the step of taking a ratio of said subsequent and initial parameters.

14. The method of claim 1, including the steps of repetitively monitoring the separation of said incubated fully suspended phase until said particle-rich phase is established, in order to generate a plurality of intermediate measured parameters.

15. The method of claim 14, including the steps of:
directing electromagnetic radiation through said container at a pair of vertically spaced apart locations in order to generate said plurality of intermediate measured parameters;
calculating a ratio of the first measurements in time at said vertically spaced apart locations, and using said ratio as a denominator with the remainder of said plurality of intermediate measured parameters until a final steady state is reached.

* * * * *